Sept. 16, 1952 M. L. WHISLER Plant Pat. 1,135
ROSE PLANT
Filed Sept. 26, 1951
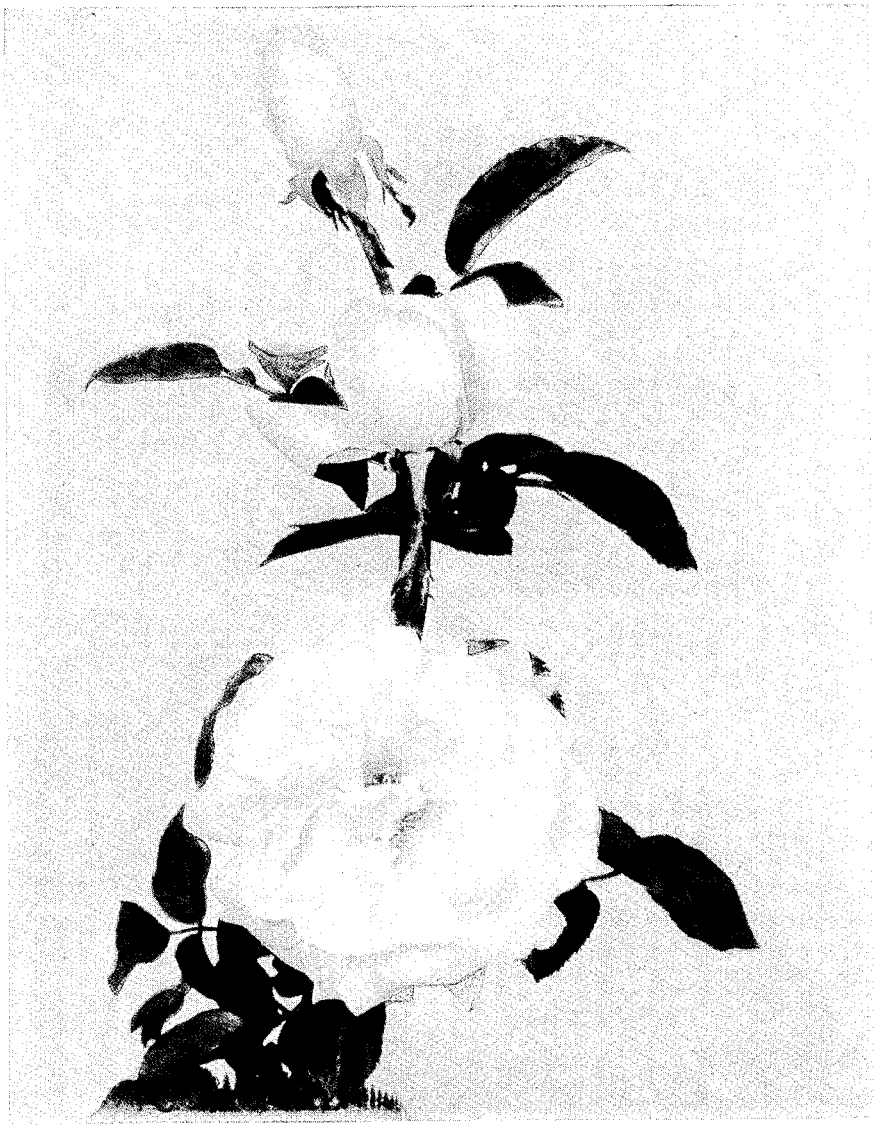
Inventor.
M. L. Whisler
By: Robbs & Cobb
Attorneys.

Patented Sept. 16, 1952

Plant Pat. 1,135

UNITED STATES PATENT OFFICE 1,135

ROSE PLANT

Milton L. Whisler, Van Nuys, Calif., assignor to Germain's, Inc., Van Nuys, Calif., a corporation of California Application September 26, 1951, Serial No. 248,294

1 Claim. (Cl. 47—61)

The present invention relates to a new and distinct variety of rose plant of the hybrid tea class, originated by me by crossing the variety "Mark Sullivan" (Plant Patent No. 599) × the variety "Sister Therese" (unpatented).

As the result of this cross, I have produced a materially improved variety which is distinguished from its parents as well as from other varieties, but which more nearly resembles the variety "Golden Rapture" (unpatented) than any other, yet is distinctly different therefrom.

The primary features of novelty and distinctiveness of the new variety are the bright yellow color of its flowers and their ability to hold their color in hot weather, and the vigor of growth of the plant which tends to produce long, strong stems on which the flowers are borne.

Asexual reproduction of this new variety by cuttings, grafting and budding at Van Nuys, California, shows that the foregoing characteristics come true to form and are established and transmitted through succeeding propagations.

The accompanying drawing shows specimens of the flowers and foliage of the new variety in different stages of development.

The following is a detailed description of the new variety, with color terminology in accordance with the Horticultural Color Chart of the British Color Council, except where general color terms of ordinary dictionary significance are obvious:

Type: Half-hardy; outdoor; seedling; for cut flowers and for garden decoration.

Class: Hybrid tea.

Breeding: Seedling.

*Seed parent.*—"Mark Sullivan."

*Pollen parent.*—"Sister Theresa."

Propagation: Holds its distinguishing characteristics through succeeding propagations by cuttings, grafting and budding.

*Flower*

Locality where grown and observed: Van Nuys, California.

Flowers borne: Singly to stem; on strong, long stems.

Quantity of bloom: Free; outdoors.

Continuity: Continuous.

Fragrance: Strong; spicy.

Bud:

*Peduncle.*—Medium length; medium size; stiff; light reddish green; numerous brown prickles.

*Before calyx breaks.*—Size—large. Form—long; ovoid; with foliaceous appendages; with slender, much cut foliaceous parts extending beyond the tip of the bud equal to ¼ of its length. Color—gray green.

*As calyx breaks.*—Color—Aureolin, Plate 3.

*As first petal opens.*—Size—large. Form—long; ovoid. Color—outside: Aureolin, Plate 3/2, inside: Aureolin, Plate 3.

*Opening.*—Opens up well.

Bloom:

*Size, when fully open.*—Medium to large; 4 inches to 5 inches.

*Petalage.*—Semi-double; from 30 to 35 petals; arranged regularly.

*Form.*—Open at first; becoming flat; remaining flat.

Petals: Thick; soft; with inside velvety and outside satiny.

*Shape.*—Outside—obovate. Intermediate—obovate.

This description of a newly opened flower was made from a rose grown outdoors in the month of August, at Van Nuys, California:

*Color.*—Outside petal—outside surface: Aureolin, Plate 3/2; inside surface: Aureolin, Plate 3/2. Intermediate petal—outside surface: Aureolin, Plate 3/1; inside surface: Aureolin, Plate 3/1. Inner petal—outside surface: Aureolin, Plate 3; inside surface: Aureolin, Plate 3.

This description was made from a rose that was open for three days outdoors in the month of August, at Van Nuys, California:

*Color.*—Outside petal—outside surface: Aureolin, Plate 3/2; inside surface: Aureolin, Plate 3/2. Inside petal—outside surface: Aureolin, Plate 3/1; inside surface: Aureolin, Plate 3/1.

*General color effect.*—Newly opened flower—Aureolin, Plate 3/1. Three days open—Aureolin, Plate 3/2.

*Behavoir.*—Drop off cleanly; retains its color very well during hot weather.

*Flower longevity.*—On bush in garden—4 4 days in August. Cut roses, grown outdoors, kept at living room temperature—3 days in August.

*Reproductive organs*

Stamens: Many; arranged regularly.
Filaments: Long most with anthers. Color—Capsicum Red, Plate 715/3.
Anthers: Medium size; all open at once. Color—Buttercup Yellow, Plate 5.
Pollen: Abundant; gold.
Pistils: Many.
Styles: Uneven; medium length; bunched.
Stigma: Yellow.
Ovaries: Some protruding from calyx.
Hips Short; flat; green-gray; moderately hairy; walls thin, dry.
Sepals: Permanent; long; recurved. Color—gray-green.

*Plant*

Foliage:

*Leaves.*—Compound of five leaflets; sparse; medium size; heavy; leathery.

*Leaflet.*—Shape—elliptic with apex acute. Base—obtuse. Margin—doubly serrate.

*Color.*—Mature—upper surface: dark green; under surface: normal green. Young—upper surface: light green; under surface: light green-bronze.

*Rachis.*—Upper side—grooved; hairy. Under side—moderately smooth; hairy.

*Stipules.*—Long; medium width; with medium length points turning out at an angle of more than 45°

*Disease.*—Resistant to mildew.

Growth:

*Habit.*—Upright; little branched.

*Growth.*—Vigorous.

*Canes.*—Heavy.

*Main* stems. — Color — dull gray-green. Thorns—several; long; with long, broad base. Prickles—none. Hairs—few.

*Branches.* — Color — dull gray - green. Thorns—several; long; straight; with long, broad base. Prickles — many; brown. Hairs—few; brown.

*New shoots.*—Color—bright green. Thorns—many; long; straight; with long, broad base. Prickles—none. Hairs—none.

I claim:

A new and distinct variety of rose plant of the hybrid tea class, substantially as herein shown and described, characterized as to novelty by the bright yellow color of its flowers and their ability to hold their color in hot weather, and by the vigor of growth of the plant and its consequent tendency to produce long, strong stems on which the flowers are borne.

MILTON L. WHISLER.

No references cited.